US012095035B2

(12) United States Patent
Li et al.

(10) Patent No.: US 12,095,035 B2
(45) Date of Patent: Sep. 17, 2024

(54) ELECTROLYTIC SOLUTION, AND ELECTROCHEMICAL DEVICE USING THE SAME

(71) Applicant: NINGDE AMPEREX TECHNOLOGY LIMITED, Ningde (CN)

(72) Inventors: Wenqiang Li, Ningde (CN); Jian Liu, Ningde (CN); Mingming Guan, Ningde (CN); Jianming Zheng, Ningde (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 888 days.

(21) Appl. No.: 17/059,701

(22) PCT Filed: Jan. 20, 2020

(86) PCT No.: PCT/CN2020/073221
§ 371 (c)(1),
(2) Date: Nov. 30, 2020

(87) PCT Pub. No.: WO2021/146839
PCT Pub. Date: Jul. 29, 2021

(65) Prior Publication Data
US 2021/0408603 A1 Dec. 30, 2021

(51) Int. Cl.
*H01M 10/0567* (2010.01)
*H01M 4/485* (2010.01)
*H01M 10/0525* (2010.01)
*H01M 10/0568* (2010.01)
*H01M 10/0569* (2010.01)
*C07D 327/10* (2006.01)
*C07D 411/04* (2006.01)
*C07D 411/14* (2006.01)
*C07D 497/04* (2006.01)

(52) U.S. Cl.
CPC ....... *H01M 10/0567* (2013.01); *H01M 4/485* (2013.01); *H01M 10/0525* (2013.01); *H01M 10/0568* (2013.01); *H01M 10/0569* (2013.01); *C07D 327/10* (2013.01); *C07D 411/04* (2013.01); *C07D 411/14* (2013.01); *C07D 497/04* (2013.01); *H01M 2300/0034* (2013.01); *H01M 2300/0037* (2013.01); *H01M 2300/004* (2013.01)

(58) Field of Classification Search
None
See application file for complete search history.

(56) References Cited

U.S. PATENT DOCUMENTS

2019/0296398 A1  9/2019  Burkhardt et al.

FOREIGN PATENT DOCUMENTS

| CN | 103098290 A | 5/2013 |
|---|---|---|
| CN | 105895955 A | 8/2016 |
| CN | 106025356 A | 10/2016 |
| CN | 108242566 | * 7/2018 |
| CN | 108242566 A | 7/2018 |
| CN | 109037776 A | 12/2018 |
| CN | 109786834 A | 5/2019 |
| CN | 109792082 A | 5/2019 |
| CN | 109792083 A | 5/2019 |
| CN | 109860703 A | 6/2019 |
| CN | 109888384 | * 6/2019 |
| CN | 109888384 A | 6/2019 |
| CN | 110021785 | * 7/2019 |
| CN | 110021785 A | 7/2019 |
| CN | 110364695 A | 10/2019 |
| EP | 3086396 | 10/2016 |
| JP | 10-189042 A | 7/1998 |
| JP | 2010015719 A | 1/2010 |
| JP | 2014222624 A | 11/2014 |
| JP | 2017-520100 A | 7/2017 |
| JP | 2018-133284 A | 8/2018 |
| JP | 2018-133332 A | 8/2018 |
| JP | 2019-521494 A | 7/2019 |
| WO | 2012/053644 A1 | 4/2012 |
| WO | 2015179205 A1 | 11/2015 |
| WO | 2015179210 A1 | 11/2015 |
| WO | 2018011062 A2 | 1/2018 |
| WO | 2018050652 A1 | 3/2018 |
| WO | 2019211353 A1 | 11/2019 |
| WO | 2019211366 A1 | 11/2019 |

OTHER PUBLICATIONS

PCT International Search Report mailed Oct. 22, 2020, in counterpart PCT application PCT/CN2020/073221, 4 pages in Chinese.
Chinese Office Action mailed Dec. 28, 2022 in counterpart Chinese application CN202010064859.4, 13 pages in Chinese.
Supple, entary European Search Report mailed Feb. 3, 2023 in counterpart European application EP20915120.8, 4 pages in English.
Japanese Office Action issued Aug. 22, 2023, in corresponding Japanese Patent Application No. 2022-544205, 4pp.
Second Chinese Office Action mailed May 12, 2023 in counterpart Chinese application CN202010064859.4, 11 pages in Chinese.

* cited by examiner

Primary Examiner — Laura Weiner
(74) Attorney, Agent, or Firm — XSENSUS LLP

(57) ABSTRACT

An electrolytic solution includes the compound of Formula I and a carboxylate compound:

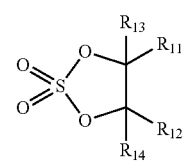

(Formula I)

The electrochemical device prepared with the electrolytic solution has reduced storage impedance, and improved post-storage swelling, overcharge performance and hot box performance.

8 Claims, No Drawings

ELECTROLYTIC SOLUTION, AND ELECTROCHEMICAL DEVICE USING THE SAME

CROSS REFERENCE TO THE RELATED APPLICATIONS

The present application is a National Stage application of PCT international application: PCT/CN2020/073221, filed on 20 Jan. 2020, the disclosure of which is hereby incorporated by reference in its entirety.

BACKGROUND

1. Field of the Invention

The present application relates to the technical field of electrochemical devices, and more particularly to an electrolytic solution and an electrochemical device using the electrolytic solution.

2. Description of the Related Art

Developing lithium-ion batteries having high energy density is a trending area of research. With the rapid development of 5G technologies and the continuous development of smart devices towards thinness and miniaturization in recent years, the resulting volume of batteries is increasing smaller, while the energy required to be provided by the batteries is increasingly higher. High voltage has provided a more effective solution and way to improve energy density, but higher voltage may be accompanied by serious safety problems. Such safety issues must be resolved so that lithium-ion batteries can be developed toward higher voltage.

The present application provides an electrolytic solution and an electrochemical device using the electrolytic solution to solve the above problems.

SUMMARY

An embodiment of the present application provides an electrolytic solution and an electrochemical device using the electrolytic solution, to solve at least one of the problems existing in related art to some extent. An embodiment of the present application also provides an electrochemical device using the electrolytic solution, and an electronic device.

In one aspect of the present application, the present application provides an electrolytic solution, which includes the compound of Formula I and a carboxylate compound:

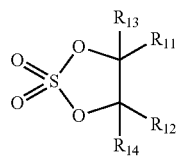

(Formula I)

where $R_{11}$, $R_{12}$, $R_{13}$, and $R_{14}$ are each independently selected from H, halogen, a cyano group, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{1-20}$ alkoxy, substituted or unsubstituted $C_{3-20}$ heterocyclic group, substituted or unsubstituted $C_{6-20}$ aryl group, substituted or unsubstituted $C_{6-20}$ heteroaryl or —$R_0$—O—R group, substituted or unsubstituted sultone, substituted or unsubstituted sulfurous acid lactone, and substituted or unsubstituted sulfuric acid lactone, where the heteroatom in the heterocyclic group and the heteroaryl is independently at least one selected from O, S, N or P at each occurrence; or $R_{11}$ and $R_{12}$, together with the carbon atoms to which they are attached, form a 5-10 membered ring structure, wherein the ring structure optionally includes a heteroatom that is at least one selected from O, S, N or P;

where $R_0$ is selected from $C_{1-6}$ alkylene group, R is selected from sulfonyl, methylsulfonyl, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{6-20}$ aryl group, or substituted or unsubstituted $C_{6-20}$ heteroaryl group;

where when $R_{11}$, $R_{12}$, $R_{13}$, $R_{14}$, and R are each independently substituted, the substituent is selected from halogen, a cyano group, sulfonyl, methylsulfonyl, $C_{1-20}$ alkyl group, $C_{3-20}$ cycloalkyl group, $C_{1-20}$ alkoxy, $C_{2-20}$ alkenyl group, $C_{6-20}$ aryl group, $C_{6-20}$ heteroaryl group, or any combination thereof.

In some embodiments, $R_{11}$, $R_{12}$, $R_{13}$, and $R_{14}$ are each independently selected from:

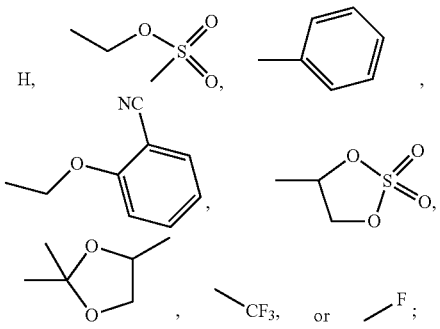

or $R_{11}$ and $R_{12}$, together with the carbon atoms to which $R_{11}$ and $R_{12}$ are attached, form

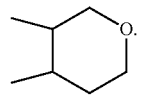

In some embodiments, the weight percentage of the compound of Formula I is a wt % based on the total weight of the electrolytic solution, where a is 0.001-5.

In some embodiments, the compound of Formula I includes at least one of the following compounds:

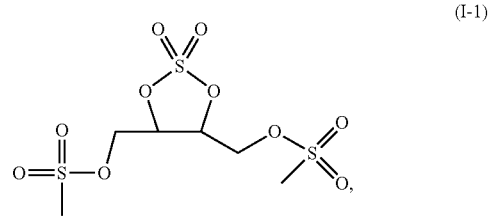

(I-1)

-continued

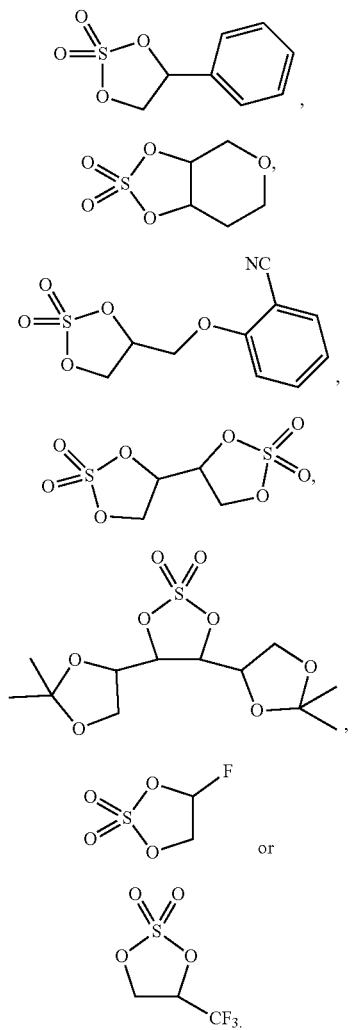

In some embodiments, the carboxylate compound includes the compound of Formula II:

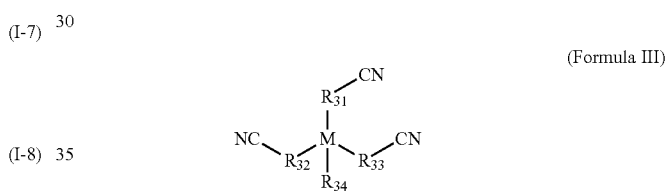

where $R_{21}$ and $R_{22}$ are each independently selected from H, halogen, a cyano group, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{1-20}$ alkoxy, substituted or unsubstituted $C_{6-20}$ aryl group, or substituted or unsubstituted $C_{6-20}$ heteroaryl group;

where when $R_{21}$ and $R_{22}$ are each independently substituted, the substituent is selected from halogen, a cyano group, $C_{1-20}$ alkyl group, $C_{3-20}$ cycloalkyl group, $C_{1-20}$ alkoxy, $C_{2-20}$ alkenyl group, $C_{6-20}$ aryl group, or any combination thereof.

In some embodiments, the weight percentage of the carboxylate compound is b wt % based on the total weight of the electrolytic solution, where b is 0.05-75.

In some embodiments, the carboxylate compound includes at least one of:

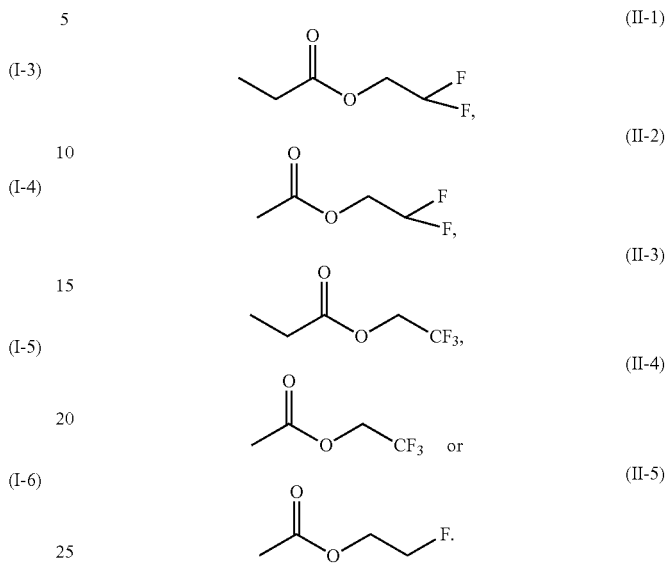

In some embodiments, the electrolytic solution further includes the compound of Formula III:

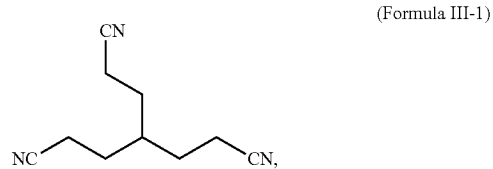

where M is C or Si;

$R_{31}$, $R_{32}$, and $R_{33}$ are each independently selected from substituted or unsubstituted $C_1$-$C_{20}$ alkylene group, substituted or unsubstituted $C_2$-$C_{20}$ alkenylene group, —$R_{35}$—S—$R_{36}$— or —$R_{37}$—O—$R_{38}$—, where $R_{35}$, $R_{36}$, $R_{37}$ and $R_{38}$ are each independently a single bond, substituted or unsubstituted $C_1$-$C_{20}$ alkylene group, or substituted or unsubstituted $C_2$-$C_{20}$ alkenylene group;

$R_{34}$ is selected from H, substituted or unsubstituted $C_1$-$C_{20}$ alkyl, or substituted or unsubstituted $C_2$-$C_{20}$ alkenyl;

where when $R_{31}$, $R_{32}$, $R_{33}$, $R_{34}$, $R_{35}$, $R_{36}$, $R_{37}$ and $R_{38}$ are each independently substituted, the substituent is selected from halogen, a cyano group, $C_{1-20}$ alkyl group, $C_{3-20}$ cycloalkyl group, $C_{1-20}$ alkoxy, $C_{2-20}$ alkenyl group, $C_{6-20}$ aryl group, or any combination thereof.

In some embodiments, the weight percentage of the compound of Formula III is 0.01-5 wt % based on the total weight of the electrolytic solution.

In some embodiments, the compound of Formula III includes at least one of the following compounds:

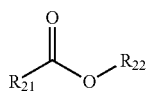

-continued

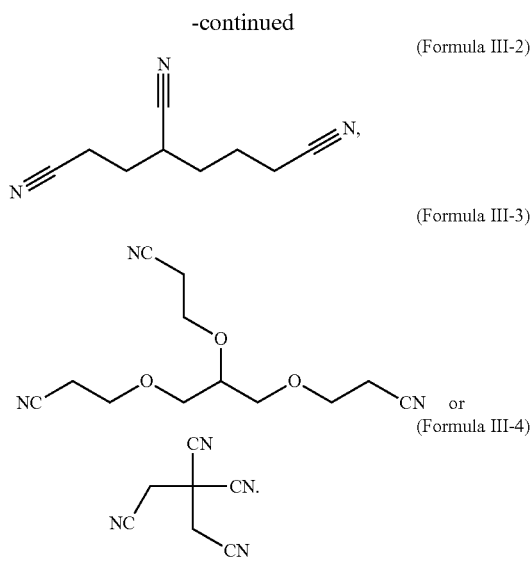

(Formula III-2)

(Formula III-3)

(Formula III-4)

In some embodiments, the electrolytic solution further includes a lithium salt additive, including at least one of $LiPO_2F_2$, lithium bis(trifluoromethanesulphonyl)imide, lithium bis(fluorosulfonyl)imide, lithium bis(oxalate)borate, lithium tetrafluorophosphate xalate, lithium difluoro(oxalate)borate, or lithium hexafluorocesate.

In some embodiments, the weight percentage of the lithium salt additive is 0.001-5 wt % based on the total weight of the electrolytic solution.

In an aspect of the present application, the present application provides an electrochemical device, which includes a cathode, having a cathode active material layer including a cathode active material; and an electrolytic solution according to an embodiment of the present application.

In some embodiments, the electrolytic solution of the electrochemical device further includes copper ions, and the content of the copper ions is 0.01-50 ppm based on the total weight of the electrolytic solution.

In some embodiments, the cathode active material includes a Ti element, and the content of the Ti element is $t \times 10^2$ ppm based on the total weight of the cathode active material layer, where t is 2-10, and meets $(a+b)/t \leq 35$.

In another aspect of the present application, the present application provides an electronic device, which includes an electrochemical device according to an embodiment of the present application.

The lithium-ion battery prepared with the electrolytic solution of the present application has reduced storage impedance, and improved storage swelling, overcharge performance and hot box performance.

Additional aspects and advantages of the embodiments of the present application will be described or shown in the following description or interpreted by implementing the embodiments of the present application.

DETAILED DESCRIPTION

The embodiments of the present application will be described in detail below. The embodiments of the present application should not be interpreted as limitations to the present application.

In the detailed description and the claims, a list of items connected by the term "one of" or similar terms may mean any of the listed items. For example, if items A and B are listed, then the phrase "one of A and B" means only A or only B. In another example, if items A, B, and C are listed, then the phrase "one of A, B and C" means only A; only B; or only C. The item A may include a single component or multiple components. The item B may include a single component or multiple components. The item C may include a single component or multiple components.

In the detailed description and the claims, a list of items connected by the term "at least one of" or similar terms may mean any combination of the listed items. For example, if items A and B are listed, then the phrase "at least one of A and B" means only A; only B; or A and B. In another example, if items A, B and C are listed, then the phrase "at least one of A, B and C" means only A; or only B; only C; A and B (excluding C); A and C (excluding B); B and C (excluding A); or all of A, B and C. The item A may include a single component or multiple components. The item B may include a single component or multiple components. The item C may include a single component or multiple components.

As used herein, the term "alkyl group" is intended to be a linear saturated hydrocarbon structure having 1 to 20 carbon atoms. The alkyl group is also intended to be a branched or cyclic hydrocarbon structure having 3 to 20 carbon atoms. For example, the alkyl group may be an alkyl group having 1-20 carbon atoms, an alkyl group having 1-10 carbon atoms, an alkyl group having 1-5 carbon atoms, an alkyl group having 5-20 carbon atoms, an alkyl group having 5-15 carbon atoms, or alkyl group having 5-10 carbon atoms. When an alkyl group having a specific number of carbon atoms is defined, it is intended to cover all geometric isomers having the carbon number. Therefore, for example, "butyl" means n-butyl, sec-butyl, isobutyl, tert-butyl and cyclobutyl; and "propyl" includes n-propyl, isopropyl and cyclopropyl. Examples of the alkyl group include, but are not limited to, methyl, ethyl, n-propyl, isopropyl, cyclopropyl, n-butyl, isobutyl, sec-butyl, tert-butyl, cyclobutyl, n-pentyl, isoamyl, neopentyl, cyclopentyl, methylcyclopentyl, ethylcyclopentyl, n-hexyl, isohexyl, cyclohexyl, n-heptyl, octyl, cyclopropyl, cyclobutyl, norbornanyl and so on. Additionally, the alkyl group can be optionally substituted.

As used herein, the term "cycloalkyl group" encompasses cyclic alkyl groups. The cycloalkyl group may be a cycloalkyl group having 3 to 20 carbon atoms, a cycloalkyl group having 6 to 20 carbon atoms, a cycloalkyl group having 3 to 12 carbon atoms, or a cycloalkyl group having 3 to 6 carbon atoms. For example, the cycloalkyl group may be cyclopropyl, cyclobutyl, cyclopentyl, cyclohexyl or the like. Additionally, the cycloalkyl group can be optionally substituted.

As used herein, the term "alkoxy" refers to a -L-O— group, where L is an alkyl group. For example, the alkoxy group may be an alkoxy group having 1-20 carbon atoms, an alkoxy group having 1-12 carbon atoms, an alkoxy group having 1-5 carbon atoms, an alkoxy group having 5-20 carbon atoms, an alkoxy group having 5-15 carbon atoms, or an alkoxy group having 5-10 carbon atoms. Additionally, the alkoxy group can be optionally substituted.

As used herein, the term "alkenyl group" refers to a monovalent unsaturated hydrocarbyl group which may be straight or branched and which has at least one and usually 1, 2 or 3 carbon-carbon double bonds. Unless otherwise defined, the alkenyl group typically contains from 2 to 20 carbon atoms, for example an alkenyl group having 2 to 20 carbon atoms, an alkenyl group having 6 to 20 carbon atoms, an alkenyl group having 2 to 12 carbon atoms or an alkenyl group having 2 to 6 carbon atoms. Representative alkenyl groups include (for example) ethenyl, n-propenyl, iso-propenyl, n-but-2-enyl, butyl-3-enyl, n-hex-3-enyl, and the like. Additionally, the alkenyl group can be optionally substituted.

As used herein, the term "alkylene group" means a linear or branched divalent saturated hydrocarbyl group. For example, the alkylene group may be an alkylene group having 1-20 carbon atoms, an alkylene group having 1-15 carbon atoms, an alkylene group having 1-10 carbon atoms, an alkylene group having 1-5 carbon atoms, an alkylene group having 5-20 carbon atoms, an alkylene group having 5-15 carbon atoms, or an alkylene is group having 5-10 carbon atoms. Representative alkylene group includes (for example) methylene, ethane-1,2-diyl ("ethylene"), propane-1,2-diyl, propane-1,3-diyl, butane-1, 4-diyl, pentane-1,5-diyl and the like. Additionally, the alkylene group can be optionally substituted.

As used herein, the term "alkenylene group" encompasses both linear and branched alkenylene groups. When an alkenylene group having a specific number of carbon atoms is defined, it is intended to cover all geometric isomers having the carbon number. For example, the alkenylene group may be an alkenylene group having 2-20 carbon atoms, an alkenylene group having 2-15 carbon atoms, an alkenylene group having 2-10 carbon atoms, an alkenylene group having 2-5 carbon atoms, an alkenylene group having 5-20 carbon atoms, an alkenylene group having 5-15 carbon atoms, or an alkenylene group having 5-10 carbon atoms. Representative alkenylene group includes (for example) ethenylene, propenylene, butenylene and the like. Additionally, the alkenylene group can be optionally substituted.

As used herein, the term "heterocyclic group" encompasses both aromatic and non-aromatic cyclic groups. Heteroaromatic cyclic groups also mean heteroaryl groups. In some embodiments, the heteroaromatic cyclic group and hetero-non-aromatic cyclic group include a $C_3$-$C_{20}$ heterocyclic group, $C_3$-$C_{150}$ heterocyclic group, $C_3$-$C_{10}$ heterocyclic group, $C_5$-$C_{20}$ heterocyclic group, $C_5$-$C_{10}$ heterocyclic group, or a $C_3$-$C_6$ heterocyclic group having at least one heteroatom. For example, morpholinyl, piperidinyl, pyrrolidinyl, and cyclic ethers, for example, tetrahydrofuran, tetrahydropyran, and the like. Additionally, the heterocyclic group can be optionally substituted.

As used herein, the term "aryl group" encompasses both monocyclic and polycyclic ring systems. A polycyclic ring may have two or more rings where two carbons are shared by two adjacent rings (where the rings are "fused"), where at least one of the rings is aromatic and other rings may be for example, a cycloalkyl group, a cycloalkenyl group, an aryl group, a heterocyclic group and/or a heteroaryl group. For example, the aryl group may be a $C_6$-$C_{50}$ aryl group, a $C_6$-$C_{40}$ aryl group, a $C_6$-$C_{30}$ aryl group, a $C_6$-$C_{20}$ aryl group, or a $C_6$-$C_{10}$ aryl group. Representative aryl group includes (for example) phenyl, methylphenyl, propylphenyl, isopropylphenyl, benzyl and naphthalen-1-yl, naphthalen-2-yl and the like. Additionally, the aryl group can be optionally substituted.

As used herein, the term "heteroaryl group" encompasses a monocyclic heteroaromatic group which may include one to three heteroatoms, for example, pyrrole, furan, thiophene, imidazole, oxazole, thiazole, triazole, pyrazole, pyridine, pyrazine, pyrimidine, and the like. The term heteroaryl group also includes a polycyclic heteroaromatic system having two or more rings in which two atoms are shared by two adjacent rings (where the ring is "fused"), in which at least one of the rings is a heteroaryl group, and other rings may be a cycloalkyl group, a cycloalkenyl group, an aryl group, a heterocyclic group and/or a heteroaryl group. The heteroatom in the heteroaryl group may be for example O, S, N, Se, and so on. For example, the heteroaryl group may be $C_3$-$C_{50}$ heteroaryl, $C_3$-$C_{40}$ heteroaryl, $C_3$-$C_{30}$ heteroaryl, $C_3$-$C_{20}$ heteroaryl, or $C_3$-$C_{10}$ heteroaryl. Additionally, the heteroaryl group can be optionally substituted.

As used herein, the term "dinitrile compound" refers to the compound having two —CN functional groups.

As used herein, the term "heteroatom" encompasses O, S, P, N, B or their isosteres.

As used herein, the term "halogen" encompasses F, Cl, Br or I.

When the above substituents are substituted, their substituents are each independently selected from the group consisting of halogen, an alkyl group, an alkenyl group, and an aryl group.

As used herein, the term "substituted" means substitution with one or more (e.g., 2, 3) substituents.

As used herein, the content of each component is calculated based on the total weight of the electrolytic solution.

I. Electrolytic Solution

In some embodiments, the present application provides an electrolytic solution, which includes the compound of Formula I and a carboxylate compound:

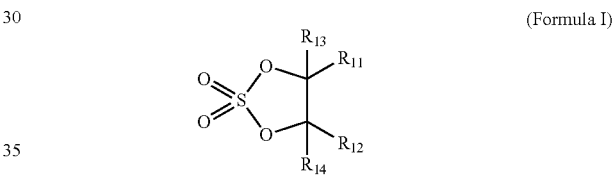

(Formula I)

where $R_{11}$, $R_{12}$, $R_{13}$, and $R_{14}$ are each independently selected from H, halogen, a cyano group, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{1-20}$ alkoxy, substituted or unsubstituted $C_{3-20}$ heterocyclic group, substituted or unsubstituted $C_{6-20}$ aryl, substituted or unsubstituted $C_{6-20}$ heteroaryl or —$R_0$—O—R group, substituted or unsubstituted sultone, substituted or unsubstituted sulfurous acid lactone, and substituted or unsubstituted sulfuric acid lactone, where the heteroatom in the heterocyclic group is at least one selected from O, S, N or P; or $R_{11}$ and $R_{12}$, together with the carbon atoms to which they are attached, form a 5-10 membered ring structure, where the ring structure optionally includes a heteroatom that is at least one selected from O, S, N or P, where the ring structure may be a saturated or unsaturated structure;

where $R_0$ is selected from $C_{1-6}$ alkylene group, R is selected from sulfonyl, methylsulfonyl, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{6-20}$ aryl group, or substituted or unsubstituted $C_{6-20}$ heteroaryl group;

where when $R_{11}$, $R_{12}$, $R_{13}$, $R_{14}$, and R are each independently substituted, the substituent is selected from halogen, a cyano group, sulfonyl, methylsulfonyl, $C_{1-20}$ alkyl group, $C_{3-20}$ cycloalkyl group, $C_{1-20}$ alkoxy, $C_{2-20}$ alkenyl group, $C_{6-20}$ aryl group, $C_{6-20}$ heteroaryl group, or any combination thereof.

In some embodiments, $R_{11}$, $R_{12}$, $R_{13}$, and $R_{14}$ are each independently selected from:

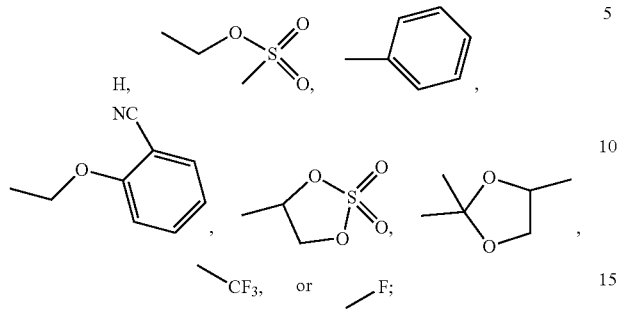

or $R_{11}$ and $R_{12}$, together with the carbon atoms to which $R_{11}$ and $R_{12}$ are attached, form

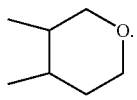

In some embodiments, the weight percentage of the compound of Formula I is a wt % based on the total weight of the electrolyte solution, where a is 0.001-5. In some embodiments, the weight percentage of the compound of Formula I is 0.001 wt %, 0.005 wt %, 0.01 wt %, 0.05 wt %, 0.1 wt %, 0.15 wt %, 0.2 wt %, 0.3 wt %, 0.4 wt %, 0.5 wt %, 0.6 wt %, 0.7 wt %, 0.8 wt %, 1 wt %, 2 wt %, 3 wt %, 3.5 wt %, 4 wt %, 4.5 wt %, 5 wt %, or within a range consisting of any two of these values, based on the total weight of the electrolyte solution. When the weight percentage of the compound of Formula I within this range, the compound of Formula I can form a better protective film, which can more effectively prevent the side reaction between the electrolyte solution and the cathode or anode.

In some embodiments, the compound of Formula I includes at least one of the following compounds or is at least one selected from the following compounds:

(I-1)

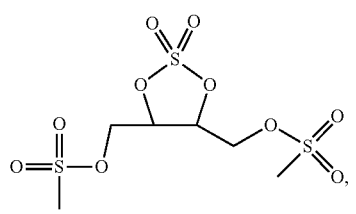

(I-2)

(I-3)

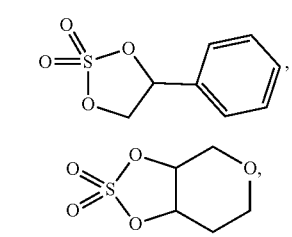

(I-4)

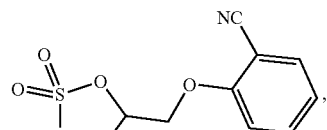

(I-5)

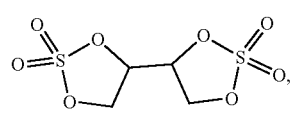

(I-6)

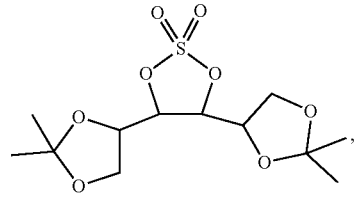

(I-7)

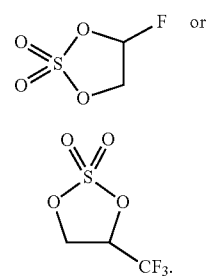

(I-8)

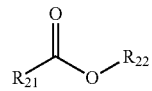

The combination of the compound of Formula I and the fluorinated carboxylate can fully exert the stability of the organic protective film and the oxidation resistance of the electrolytic solution, and can effectively improve the hot box and overcharge performance. The detailed mechanism underlying this effect is unknown, and may be considered as follows: the compound of Formula I and the fluorinated carboxylate work together to improve the oxidation resistance of the electrolytic solution system. This is more conducive to the film formation from the additives on the cathode and anode, thereby effectively protecting the active material. As the temperature rises, the protection of the organic protective film for the active material will be gradually weakened. The compound of Formula I and the fluorinated carboxylate work together to effectively reduce chemical heat production and improve the safety of the electrochemical device.

In some embodiments, the carboxylate compound includes or is selected from the compound of Formula II:

(Formula II)

$$R_{21}\underset{O}{\overset{O}{\|}}C-O-R_{22}$$

where $R_{21}$ and $R_{22}$ are each independently selected from H, halogen, a cyano group, substituted or unsubstituted $C_{1-20}$ alkyl group, substituted or unsubstituted $C_{3-20}$ cycloalkyl group, substituted or unsubstituted $C_{2-20}$ alkenyl group, substituted or unsubstituted $C_{1-20}$ alkoxy, substituted or unsubstituted $C_{6-20}$ aryl group, or substituted or unsubstituted $C_{6-20}$ heteroaryl group;

where when $R_{21}$ and $R_{22}$ are each independently substituted, the substituent is selected from halogen, a cyano group, $C_{1-20}$ alkyl group, $C_{3-20}$ cycloalkyl group, $C_{1-20}$ alkoxy, $C_{2-20}$ alkenyl group, $C_{6-20}$ aryl group, or any combination thereof.

In some embodiments, the weight percentage of the carboxylate compound is b wt % based on the total weight of the electrolytic solution, where b is 0.05-75. In some embodiments, the weight percentage of the carboxylate compound is 0.05 wt %, 0.1 wt %, 0.5 wt %, 1 wt %, 3 wt %, 5 wt %, 10 wt %, 15 wt %, 20 wt %, 25 wt %, 30 wt %, 35 wt %, 40 wt %, 45 wt %, 50 wt %, 55 wt %, 55 wt %, 60 wt %, 65 wt %, 70 wt %, 75 wt %, or within a range consisting of any two of these values, based on the total weight of the electrolytic solution. When the weight percentage of the carboxylate is within this range, the electrochemical device has better overcharge performance and hot box performance.

In some embodiments, the carboxylate compound includes at least one of the following compounds or is at least one selected from the following compounds:

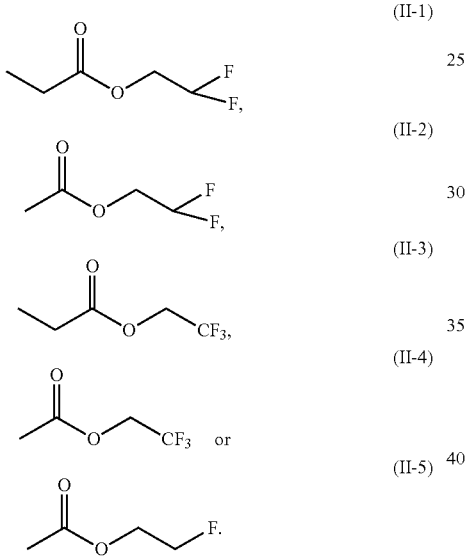

In some embodiments, the electrolytic solution further includes the compound of Formula III:

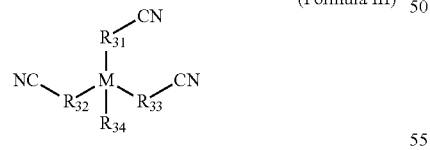

where M is one of C or Si;

$R_{31}$, $R_{32}$, and $R_{33}$ are each independently selected from substituted or unsubstituted $C_1$-$C_{20}$ alkylene group, substituted or unsubstituted $C_2$-$C_{20}$ alkenylene group, —$R_{35}$—S—$R_{36}$— or —$R_{37}$—O—$R_{38}$—, where $R_{35}$, $R_{36}$, $R_{37}$ and $R_{38}$ are each independently a single bond, substituted or unsubstituted $C_1$-$C_{20}$ alkylene group, or substituted or unsubstituted $C_2$-$C_{20}$ alkenylene group;

$R_{34}$ is selected from H, substituted or unsubstituted $C_1$-$C_{20}$ alkyl group, or substituted or unsubstituted $C_2$-$C_{20}$ alkenyl group;

where when $R_{31}$, $R_{32}$, $R_{33}$, $R_{34}$, $R_{35}$, $R_{36}$, $R_{37}$ and $R_{38}$ are each independently substituted, the substituent is selected from halogen, a cyano group, $C_{1-20}$ alkyl group, $C_{3-20}$ cycloalkyl group, $C_{1-20}$ alkoxy, $C_{2-20}$ alkenyl group, $C_{6-20}$ aryl group, or any combination thereof.

The compound of Formula I, the carboxylate compound and the compound of Formula III work together to further improve the overcharge performance of the electrochemical device and also improve the swelling problem during high-temperature storage of the electrochemical device. The detailed mechanism underlying this effect is unknown, it can be considered as follows: the compound of Formula I, the carboxylate compound and the compound of Formula III work together to further reduce the risk of oxidation of the electrolytic solution, and also improve the protection for the cathode and reduce the direct contact between the cathode active material interface with the electrolytic solution, thereby alleviating the swelling caused by the contact between the electrolytic solution and the cathode active material during high-temperature storage.

In some embodiments, the weight percentage of the compound of Formula III is 0.01-5 wt % based on the total weight of the electrolytic solution. In some embodiments, the weight percentage of the compound of Formula III is 0.01 wt %, 0.05 wt %, 0.1 wt %, 0.5 wt %, 1 wt %, 1.5 wt %, 2 wt %, 2.5 wt %, 3 wt %, 3.5 wt %, 4 wt %, 4.5 wt %, 5 wt %, or within a range consisting of any two of these values, based on the total weight of the electrolytic solution. When the weight percentage of the compound of Formula III is within this range, a better overcharge performance and high-temperature storage performance can be achieved.

In some embodiments, the compound of Formula III includes at least one of the following compounds or is at least one selected from the following compounds:

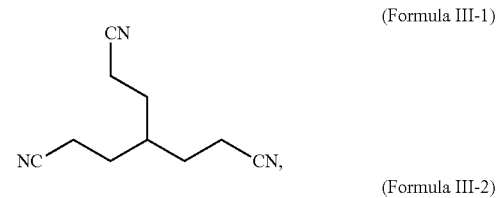

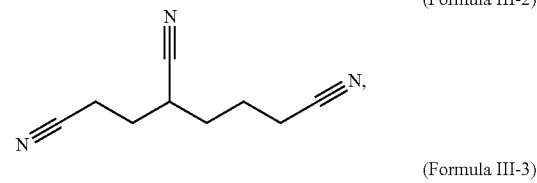

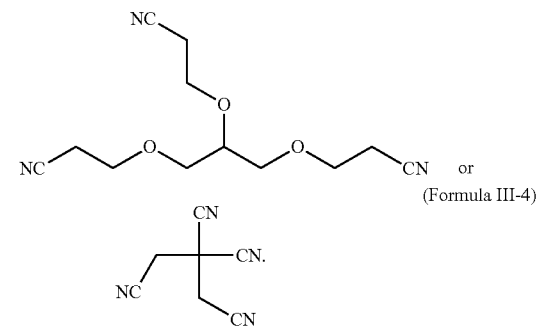

In some embodiments, the electrolytic solution further includes a lithium salt additive, including at least one of $LiPO_2F_2$, lithium bis(trifluoromethanesulphonyl)imide, lithium bis(fluorosulfonyl)imide, lithium bis(oxalate)borate, tetrafluorophosphate xalate, lithium difluoro(oxalate)borate, or lithium hexafluorocesate.

In some embodiments, the weight percentage of the lithium salt additive is about 0.001-5 wt % based on the total weight of the electrolytic solution. In some embodiments, the weight percentage of the lithium salt additive is 0.001 wt %, 0.005 wt %, 0.01 wt %, 0.05 wt %, 0.1 wt %, 0.5 wt %, 1 wt %, 1.5 wt %, 1.5 wt %, 2 wt %, 2.5 wt %, 3 wt %, 3.5 wt %, 4 wt %, 4.5 wt %, 5 wt %, or within a range consisting of any two of these values, based on the total weight of the electrolytic solution.

In some embodiments, the electrolytic solution further includes a dinitrile compound. Due to the low steric hindrance, the dinitrile compound can make up the film formation deficiency of the compound of Formula III and enhance the interface protection for the cathode active material.

In some embodiments, the dinitrile compound includes, but is not limited to: succinonitrile, glutaronitrile, adiponitrile, 1,5-dicyanopentane, 1,6-dicyanohexane, 1,7-dicyanoheptane, 1,8-dicyanooctane, 1,9-dicyanononane, 1,10-dicyanodecane, 1,12-dicyanododecane, tetramethylsuccinonitrile, 2-methylglutaronitrile, 2,4-dimethylglutaronitrile, 2,2,4,4-tetramethylglutaronitrile, 1,4-dicyanopentane, 1,4-dicyanopentane, 2,5-dimethyl-2,5-hexane dicarbonitrile, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,5-dioxa-pimelonitrile, 1,4-bis(cyanoethoxy)butane, ethylene glycol bis(2-cyanoethyl)ether, diethylene glycol bis(2-cyanoethyl)ether, triethylene glycol bis(2-cyanoethyl)ether, tetraethylene glycol bis(2-cyanoethyl)ether, 3,6,9,12,15,18-hexaoxaeicosoic acid dinitrile, 1,3-bis(2-cyanoethoxy)propane, 1,4-bis(2-cyanoethoxy)butane, 1,5-bis(2-cyanoethoxy)pentane, ethylene glycol bis(4-cyanobutyl)ether, 1,4-dicyano-2-butene, 1,4-dicyano-2-methyl-2-butene, 1,4-dicyano-2-ethyl-2-butene, 1,4-dicyano-2,3-dimethyl-2-butene, 1,4-dicyano-2,3-diethyl-2-butene, 1,6-dicyano-3-hexene, 1,6-dicyano-2-methyl-3-hexene, or 1,6-dicyano-2-methyl-5-methyl-3-hexene.

In some embodiments, the weight percentage of the dinitrile compound is 0.1-15 wt % based on the total weight of the electrolytic solution. In some embodiments, the weight percentage of the dinitrile compound is no less than 0.1 wt % based on the total weight of the electrolytic solution. In some embodiments, the weight percentage of the dinitrile compound is no less than 0.5 wt % based on the total weight of the electrolytic solution. In some embodiments, the weight percentage of the dinitrile compound is no less than 2 wt % based on the total weight of the electrolytic solution. In some embodiments, the weight percentage of the dinitrile compound is no less than 4 wt % based on the total weight of the electrolytic solution. In some embodiments, the weight percentage of the dinitrile compound is not greater than 15 wt % based on the total weight of the electrolytic solution. In some embodiments, the weight percentage of the dinitrile compound is not greater than 10 wt % based on the total weight of the electrolytic solution. In some embodiments, the weight percentage of the dinitrile compound is not greater than 8 wt % based on the total weight of the electrolytic solution.

In some embodiments, the electrolytic solution further includes a cyclic ether. The cyclic ether can form a film on both the cathode and the anode, reducing the reaction between the electrolytic solution and the active material.

In some embodiments, the cyclic ether includes, but is not limited to, tetrahydrofuran, 2-methyltetrahydrofuran, 1,3-dioxolane, 2-methyl 1,3-dioxolane, 4-methyl 1,3-dioxolane, 1,3-dioxane, 1,4-dioxane and dimethoxypropane.

In some embodiments, the weight percentage of the cyclic ether is 0.1-10 wt % based on the total weight of the electrolytic solution. In some embodiments, the weight percentage of the cyclic ether is no less than 0.1 wt % based on the total weight of the electrolytic solution. In some embodiments, the weight percentage of the cyclic ether is no less than 0.5 wt % based on the total weight of the electrolytic solution. In some embodiments, the weight percentage of the cyclic ether is not greater than 2 wt % based on the total weight of the electrolytic solution. In some embodiments, the weight percentage of the cyclic ether is not greater than 5 wt % based on the total weight of the electrolytic solution.

In some embodiments, the electrolytic solution further includes a chain ether. In some embodiments, the chain ether includes, but is not limited to, dimethoxymethane, 1,1-dimethoxyethane, 1,2-dimethoxyethane, diethoxymethane, 1,1-diethoxyethane, 1,2-diethoxyethane, ethoxymethoxymethane, 1,1-ethoxymethoxyethane and 1,2-ethoxymethoxyethane.

In some embodiments, the weight percentage of the chain ether is 0.1-10 wt % based on the total weight of the electrolytic solution. In some embodiments, the weight percentage of the chain ether is no less than 0.5 wt % based on the total weight of the electrolytic solution. In some embodiments, the weight percentage of the chain ether is no less than 2 wt % based on the total weight of the electrolytic solution. In some embodiments, the weight percentage of the chain ether is no less than 3 wt % based on the total weight of the electrolytic solution. In some embodiments, the weight percentage of the chain ether is not greater than 10 wt % based on the total weight of the electrolytic solution. In some embodiments, the weight percentage of the chain ether is not greater than 5 wt % based on the total weight of the electrolytic solution.

In some embodiments, the electrolytic solution further includes a phosphorus containing organic solvent. In some embodiments, the phosphorus containing organic solvent includes, but is not limited to, trimethyl phosphate, triethyl phosphate, dimethyl ethyl phosphate, methyl diethyl phosphate, ethylene methyl phosphate, ethylene ethyl phosphate, triphenyl phosphate, trimethyl phosphite, triethyl phosphite, triphenyl phosphite, tris(2,2,2-trifluoroethyl) phosphate and tris(2,2,3,3,3-pentafluoropropyl) phosphate.

In some embodiments, the weight percentage of the phosphorus containing organic solvent is 0.1-10 wt % based on the total weight of the electrolytic solution. In some embodiments, the weight percentage of the phosphorus containing organic solvent is no less than 0.1 wt % based on the total weight of the electrolytic solution. In some embodiments, the weight percentage of the phosphorus containing organic solvent is no less than 0.5 wt % based on the total weight of the electrolytic solution. In some embodiments, the weight percentage of the phosphorus containing organic solvent is not greater than 2 wt % based on the total weight of the electrolytic solution. In some embodiments, the weight percentage of the phosphorus containing organic solvent is not greater than 3 wt % based on the total weight of the electrolytic solution. In some embodiments, the weight percentage of the phosphorus containing organic solvent is not greater than 5 wt % based on the total weight of the electrolytic solution.

In some embodiments, the electrolytic solution further includes an aromatic fluorine-containing organic solvent. The aromatic fluorine-containing solvent can quickly form a film to protect the active material, and the fluorine-containing substance can improve the infiltration of the electrolytic solution to the active material. In some embodiments, the aromatic fluorine-containing organic solvent includes, but is not limited to, fluorobenzene, difluorobenzene, trifluorobenzene, tetrafluorobenzene, pentafluorobenzene, hexafluorobenzene, and trifluoromethylbenzene.

In some embodiments, the weight percentage of the aromatic fluorine-containing solvent is about 0.1-10 wt % based on the total weight of the electrolytic solution. In some embodiments, the weight percentage of the aromatic fluorine-containing solvent is no less than 0.5 wt % based on the total weight of the electrolytic solution. In some embodiments, the weight percentage of the aromatic fluorine-containing solvent is no less than 2 wt % based on the total weight of the electrolytic solution. In some embodiments, the weight percentage of the aromatic fluorine-containing solvent is not greater than 4 wt % based on the total weight of the electrolytic solution. In some embodiments, the weight percentage of the aromatic fluorine-containing solvent is not greater than 8 wt % based on the total weight of the electrolytic solution.

II. Electrolyte

The electrolyte used in the electrolyte solution according to the embodiments of the present application may be an electrolyte known in the prior art, including, but not limited to, an inorganic lithium salt, such as $LiClO_4$, $LiAsF_6$, $LiPF_6$, $LiBF_4$, $LiSbF_6$, $LiSO_3F$, and $LiN(FSO_2)_2$; a fluorine-containing organic lithium salt, such as $LiCF_3SO_3$, $LiN(FSO_2)(CF_3SO_2)$, $LiN(CF_3SO_2)_2$, $LiN(C_2F_5SO_2)_2$, cyclic lithium 1,3-hexafluoropropane disulfonimide, cyclic lithium 1,2-tetrafluoroethane disulfonimide, $LiN(CF_3SO_2)(C_4F_9SO_2)$, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_2(CF_3)_2$, $LiBF_2(C_2F_5)_2$, $LiBF_2(CF_3SO_2)_2$, and $LiBF_2(C_2F_5SO_2)_2$; and a lithium salt containing a dicarboxylic acid complex, such as lithium bis(oxalato)borate, lithium difluoro(oxalato)borate, lithium tris(oxalato)phosphate, lithium difluorobis(oxalato)phosphate, and lithiumtetrafluoro(oxalato)phosphate. Additionally, the electrolytic solution may be used alone or in combination of two or more thereof. For example, in some embodiments, the electrolytic solution includes a combination of $LiPF_6$ and $LiBF_4$. In some embodiments, the electrolytic solution includes a combination of an inorganic lithium salt such as $LiPF_6$ or $LiBF_4$ and a fluorine-containing organic lithium salt such as $LiCF_3SO_3$, $LiN(CF_3SO_2)_2$, and $LiN(C_2F_5SO_2)_2$. In some embodiments, the concentration of the electrolytic solution is in the range of 0.8-3 mol/L, for example, 0.8-2.5 mol/L, 0.8-2 mol/L, 1-2 mol/L, 0.5-1.5 mol/L, 0.8-1.3 mol/L, 0.5-1.2 mol/L, such as 1 mol/L, 1.15 mol/L, 1.2 mol/L, 1.5 mol/L, 2 mol/L or 2.5 mol/L.

III. Electrochemical Device

The electrochemical device of the present application includes any device where an electrochemical reaction takes place, and specific examples include all kinds of primary batteries, secondary batteries, fuel cells, solar cells, or capacitors. In particular, the electrochemical device is a lithium secondary battery including a lithium metal secondary battery, a lithium ion secondary battery, a lithium polymer secondary battery or a lithium ion polymer secondary battery. In some embodiments, the electrochemical device of the present application is an electrochemical device having a cathode having a cathode active material capable of absorbing and releasing metal ions; an anode having an anode active material capable of absorbing and releasing metal ions, and characterized by including an electrolytic solution according to any embodiment of the present application.

1. Electrolytic Solution

The electrolytic solution used in the electrochemical device of the present application is an electrolytic solution according to any embodiment of the present application.

In some embodiments, the electrolytic solution of the electrochemical device according to the present application further includes copper ions, and the content of the copper ions is 0.01-50 ppm based on the total weight of the electrolytic solution. In some embodiments, the content of copper ions is 0.01 ppm, 0.05 ppm, 0.1 ppm, 0.5 ppm, 1 ppm, 2 ppm, 3 ppm, 4 ppm, 5 ppm, 7 ppm, 10 ppm, 15 ppm, 20 ppm, 25 ppm, 30 ppm, 35 ppm, 40 ppm, 45 ppm, 50 ppm, or within a range consisting of any two of these values, based on the total weight of the electrolytic solution.

Moreover, the electrolytic solution used in the electrochemical device of the present application may include other electrolytic solutions falling within the scope of present application.

2. Anode

The anode material used in the electrochemical device of the present application, and the construction and manufacturing methods therefor are not particularly limited, and may be any of the techniques disclosed in the prior art. In some embodiments, the anode may be one described in U.S. Pat. No. 9,812,739B, which is incorporated herein by reference to its entirety.

In some embodiments, the anode includes a current collector and an anode active material layer on the current collector. The anode active material includes a material that reversibly intercalates/deintercalates lithium ions. In some embodiments, the material that reversibly intercalates/deintercalates lithium ions includes a carbon material. In some embodiments, the carbon material may be any carbon-based anode active material commonly used in lithium ion rechargeable batteries. In some embodiments, the carbon material includes, but is not limited to, crystalline carbon, amorphous carbon, or a mixture thereof. The crystalline carbon may be amorphous or flake-shaped, small flake-shaped, spherical or fibrous natural graphite or artificial graphite. The amorphous carbon may be soft carbon, hard carbon, mesophase pitch carbide, calcined coke, and the like.

In some embodiments, the anode active material layer includes an anode active material. In some embodiments, the anode active material includes, but is not limited to, lithium metal, structured lithium metal, natural graphite, artificial graphite, mesocarbon microbead (MCMB), hard carbon, soft carbon, silicon, silicon-carbon composite, Li—Sn alloy, Li—Sn—O alloy, Sn, SnO, $SnO_2$, lithiated $TiO_2$—$Li_4Ti_5O_{12}$ having spinel structure, Li—Al alloy and any combination thereof.

When the anode includes a silicon-carbon compound, based on the total weight of the anode active material, silicon:carbon=1:10-10:1, and the median diameter D50 of the silicon-carbon compound is 0.1 μm-100 μm. When the anode includes an alloy material, an anode active material layer can be formed by vapor deposition, sputtering, or plating. When the anode includes lithium metal, an anode active material layer is formed by for example a conductive skeleton of twisted spherical shape and metal particles dispersed in the conductive skeleton. In some embodiments, the conductive skeleton of twisted spherical shape may have a porosity of 5% to 85%. In some embodiments, a protective layer may be further disposed on the anode active material layer of lithium metal.

In some embodiments, the anode active material layer includes a binder, and optionally a conductive material. The binder increases the binding of the anode active material particles to each other and the binding of the anode active material to the current collector. In some embodiments, the binder includes, but is not limited to, polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, or a mixture thereof. In some embodiments, the carbon-based material is selected from natural graphite, artificial graphite, carbon black, acetylene black, Ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector include, but is not limited to, copper foil, nickel foil, stainless steel foil, titanium foil, foamed nickel, foamed copper, polymeric substrates coated with a conductive metal, and any combinations thereof.

The anode can be produced by a production method well known in the art. For example, the anode can be obtained by mixing an active material, a conductive material and a binder in a solvent to prepare an active material composition, and coating the active material composition on a current collector. In some embodiments, the solvent may include, but is not limited to, water.

3. Cathode

The cathode material used in the electrochemical device of the present application can be prepared using materials, construction and manufacturing methods well known in the art. In some embodiments, the cathode of the present application can be prepared using the technique described in U.S. Pat. No. 9,812,739B, which is incorporated herein by reference to its entirety.

In some embodiments, the cathode includes a current collector and a cathode active material layer on the current collector. The cathode active material includes at least one lithiated intercalation compound that reversibly intercalates and deintercalates lithium ions. In some embodiments, the cathode active material includes a composite oxide. In some embodiments, the composite oxide contains lithium and at least one element selected from the group consisting of cobalt, manganese, and nickel.

In some embodiments, the cathode active material is selected from lithium cobalt oxide ($LiCoO_2$), lithium nickel cobalt manganese (NCM) ternary material, lithium iron phosphate ($LiFePO_4$), lithium manganese oxide ($LiMn_2O_4$) or any combinations thereof.

In some embodiments, the cathode active material may have a coating on its surface or may be mixed with another compound having a coating. The coating may include at least one coating element compound selected from the group consisting of an oxide of a coating element, a hydroxide of a coating element, an oxyhydroxide of a coating element, an oxycarbonate of a coating element, and a hydroxycarbonate of a coating element. The compound used for the coating may be amorphous or crystalline.

In some embodiments, the coating element contained in the coating may include Mg, Al, Co, K, Na, Ca, Si, V, Sn, Ge, Ga, B, As, Zr, F or any combinations thereof. The coating can be applied by any method as long as the method does not adversely affect the performance of the cathode active material. For example, the method may include any coating method known in the art, such as spraying, dipping, and others.

In some embodiments, the cathode active material includes a Ti element, and the content of the Ti element is $t \times 10^2$ ppm based on the total weight of the cathode active material layer, where t is 2-10, and meets $(a+b)/t \leq 35$.

In some embodiments, t is 2, 3, 4, 5, 6, 7, 8, 9, 10 or in a range consisting of any two of these values.

In some embodiments, $(a+b)/t$ is 35, 30, 25, 20, 15, 10, 15, 10, 5, 1, 0.5, 0.4, 0.3, or within a range consisting of any two of these values.

In some embodiments, the cathode active material layer further includes a binder, and optionally a conductive material. The binder increases the binding of the cathode active material particles to each other and the binding of the cathode active material to the current collector.

In some embodiments, the binder includes, but is not limited to, polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, and a mixture thereof. In some embodiments, the carbon-based material is selected from natural graphite, artificial graphite, carbon black, acetylene black, Ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the current collector may be, but is not limited to, aluminum.

The cathode can be prepared by a preparation method well known in the art. For example, the cathode can be obtained by mixing an active material, a conductive material and a binder in a solvent to prepare an active material composition, and coating the active material composition on a current collector. In some embodiments, the solvent may include, but is not limited to, N-methylpyrrolidone or the like.

In some embodiments, the cathode is prepared by forming a cathode material with a cathode active material layer including a lithium-transition metal compound powder and a binder on a current collector.

In some embodiments, the cathode active material layer can generally be produced by dry mixing a cathode material and a binder (and a conductive material and a thickener if needed) to form flakes, and pressing the obtained flakes on a cathode current collector; or dissolving or dispersing the material in a liquid medium to form a slurry, coating the slurry on a cathode current collector, and drying. In some embodiments, the material of the cathode active material layer includes any material known in the art.

4. Separator

In some embodiments, the electrochemical device of the present application is provided with a separator between the cathode and the anode to prevent short circuit. The material and shape of the separator used in the electrochemical device of the present application are not particularly limited, and may be any of the techniques disclosed in the prior art. In some embodiments, the separator includes a polymer or an inorganic substance or the like formed of a material which is stable against the electrolytic solution of the present application.

For example, the separator may include a substrate layer and a surface treatment layer. The substrate layer is a non-woven fabric, film, or composite film having a porous structure, and the material of the substrate layer is at least one selected from the group consisting of polyethylene, polypropylene, polyethylene terephthalate, and polyimide. Particularly, a porous polypropylene film, a porous polyethylene film, a polypropylene nonwoven fabric, a polyethylene nonwoven fabric, and a porous polypropylene-polyethylene-polypropylene composite film may be used.

At least one surface of the substrate layer is provided with a surface treatment layer, which may be a polymer layer or an inorganic layer, or a layer formed by mixing a polymer and an inorganic material. The ratio of the thickness of the substrate layer to the thickness of the surface treatment layer is 1:1 to 20:1, the thickness of the substrate layer is 4 to 14 μm, and the thickness of the surface treatment layer is 1 to 5 μm.

The inorganic layer includes inorganic particles and a binder. The inorganic particles are at least one selected from the group consisting of alumina, silica, magnesia, titania, hafnium dioxide, tin oxide, cerium dioxide, nickel oxide, zinc oxide, calcium oxide, zirconia, yttria, silicon carbide, eboehmite, aluminum hydroxide, magnesium hydroxide, calcium hydroxide and barium sulfate, or a combination of more than one thereof. The binder is one selected from the group consisting of polyvinylidene fluoride, a copolymer of vinylidene fluoride-hexafluoropropylene, a polyamide, polyacrylonitrile, a polyacrylate ester, polyacrylic acid, a polyacrylate salt, polyvinylpyrrolidone, polyvinyl ether, polymethyl methacrylate, polytetrafluoroethylene, and polyhexafluoropropylene, or a combination of more than one thereof. The polymer layer contains a polymer, and the material of the polymer includes at least one of a polyamide, polyacrylonitrile, a polyacrylate ester, polyacrylic acid, a polyacrylate salt, polyvinylpyrrolidone, polyvinyl ether, polyvinylidene fluoride or poly (vinylidene fluoride-hexafluoropropylene).

IV. Application

The electrolytic solution according to the embodiments of the present application can be used to reduce the storage impedance of the battery, the capacity retention rate after storage at normal temperature, the cycle and high-temperature storage performance, the overcharge performance, and the hot box performance, and is thus applicable to an electronic device including an electrochemical device.

The use of the electrochemical device according to the present application is not particularly limited, and can be used in various known applications, such as notebook computers, pen-input computers, mobile computers, e-book players, portable phones, portable fax machines, portable copiers, portable printers, head-mounted stereo headphones, video recorders, LCD TVs, portable cleaners, portable CD players, minidisc players, transceivers, electronic notebooks, calculators, memory cards, portable recorders, radios, backup power sources, motors, vehicles, motorcycles, scooters, bicycles, lighting apparatus, toys, game consoles, clocks, electric tools, flash lights, cameras, large batteries for household use, or lithium ion capacitors.

Hereinafter, a lithium ion battery is taken as an example and the preparation and performance of a lithium ion battery according to the present application is described in conjunction with specific examples of preparing the electrolytic solution of the present application and methods for testing the electrochemical device. Those skilled in the art will understand that the preparation methods described in the present application are merely exemplary, and any other suitable preparation methods also fall within the protection scope of the present application.

Although a lithium ion battery is exemplified above, other suitable electrochemical devices that the cathode material of the present application can be used therewith may occur to those skilled in the art after reading this application. Such electrochemical devices include any device in which an electrochemical reaction takes place, and specific examples include all kinds of primary batteries, secondary batteries, fuel cells, solar cells, or capacitors. In particular, the electrochemical device is a lithium secondary battery including a lithium metal secondary battery, a lithium ion secondary battery, a lithium polymer secondary battery or a lithium ion polymer secondary battery.

EXAMPLES

Hereinafter, the present application will be specifically described by way of examples and comparative examples; however, the present application is not limited thereto as long as they do not deviate from the spirit of the present application.

1. Preparation of a Lithium-Ion Battery
1) Preparation of an Electrolytic Solution In a glove box under an argon atmosphere with a moisture content of <10 ppm, ethylene carbonate (EC), diethyl carbonate (DEC), and propylene carbonate (PC) were mixed uniformly according to a weight ratio of 3:4:3. Then a sufficiently dried lithium salt $LiPF_6$ was dissolved in the mixed solvent, to obtain a basic electrolytic solution where the concentration of $LiPF_6$ was 1 mol/L. Different amounts of materials shown in the Tables below were added to the basic electrolytic solution to obtain the electrolytic solutions of various examples and comparative examples. The weight percentages of each substance in the electrolytic solution described below were calculated based on the total weight of the electrolytic solution.

Examples of the compound of Formula I include:

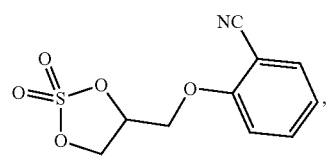
(I-4)

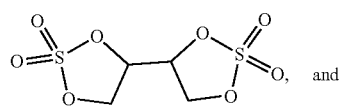
(I-5)
and

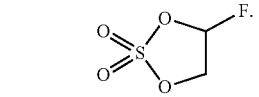
(I-7)

Examples of the carboxylate compound include:

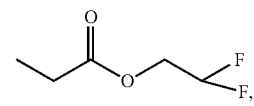
(Formula II-1)

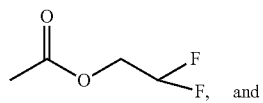
(Formula II-2)

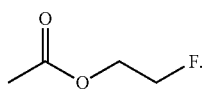
(II-5)

Examples of the compound of Formula III include:

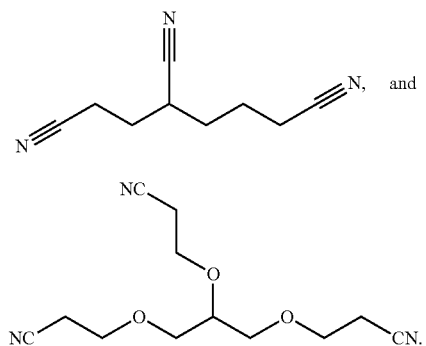
(Formula III-2)

(Formula III-3)

2) Preparation of a Cathode

The cathode active material lithium cobalt oxide (molecular formula being $LiCoO_2$) containing the Ti element, acetylene black, and the binder polyvinylidene fluoride (PVDF) were fully stirred and mixed in a suitable amount of N-methylpyrrolidone (NMP) as a solvent according to a weight ratio of 96:2:2, to form a uniform cathode slurry. The slurry was coated on a current collector Al foil of the cathode, dried, and cold-pressed to obtain a cathode active material layer. After cutting and welding with a tab, a cathode was obtained. The cathode active material lithium cobalt oxide contains a Ti element. Unless otherwise particularly specified, in the following examples and comparative examples, the content of the Ti element is 400 ppm based on the total weight of the cathode active material layer.

The following example illustrates the preparation method of a cathode active material lithium cobalt oxide containing a Ti element, wherein the content of the Ti element is 400 ppm based on the total weight of the cathode active material layer: $CoCl_2$ and $TiCl_4$ were respectively formulated into an aqueous solution, and mixed according to a molar ratio of 1:n ($0 \leq n \leq 0.00081787$) of active substances. A $NH_3 \cdot HCO_3$ solution was added to adjust the pH of mixture to 10.5, and a precipitate was obtained. The obtained precipitate was calcined at 400° C. for 5 hr to obtain $Co_3O_4$ containing a Ti element. The obtained $Co_3O_4$ was mixed uniformly with $Li_2CO_3$ according to a molar ratio of 2:3.15, and calcined at 1000° C. for 8 hrs to obtain $LiCoO_2$. $TiO_2$ was added to the obtained $LiCoO_2$ according to a molar ratio of 1:(0.00081787−n), mixed uniformly, and sintered at 800° C. for 8 hr to obtain the cathode active material lithium cobalt oxide ($LiCoO_2$) containing the Ti element.

3) Preparation of an Anode

The anode active material graphite, the conductive agent acetylene black, the binder styrene-butadiene rubber (SBR), and the thickener carboxymethylcellulose sodium (CMC) were fully mixed and stirred according to a weight ratio of 95:2:2:1 in a suitable amount of deionized water as a solvent to form a uniform anode slurry. The slurry was coated on an anode current collector Cu foil, dried, and cold pressed to obtain an anode active material layer. After cutting and welding with a tab, an anode was obtained.

4) Separator: a 7.5-8.5 μm polyethylene (PE) porous polymer film was used as a substrate. The substrate had an $Al_2O_3$ particle layer thereon, and the thickness of the $Al_2O_3$ particle layer was 2-4 μm.

5) Preparation of the lithium ion battery: The cathode, the separator, and the anode were laminated in order such that the separator was placed between and served to separate the cathode and the anode. Then, the system was wound up, and placed in an outer packaging foil. The electrolyte solution prepared above was injected into the dried battery, and after vacuum packaging, standing, formation, shaping, and other procedures, the preparation of the lithium ion battery was completed. The electrolyte solution of the lithium ion battery contains Cu ions. Unless otherwise particularly specified, the content of the Cu ions in the following examples and comparative examples is 4 ppm.

2. Performance Test Processes of a Lithium Ion Battery

1) Overcharge Test

The battery was discharged to 3.0 V at a current of 0.5 C, allowed to stand for 5 min, then charged to 6.5 V at a current of 3 C, and charged for 1 hr at a constant voltage of 6.5 V. The battery passed the test if no fire or explosion occurred. Five batteries in each Example or Comparative Example were tested, and the number of batteries that passed the test was recorded.

2) Hot Box Test

The battery was discharged to 3.0 V at a current of 0.5 C, allowed to stand for 5 min, then charged to 4.4 V at a current of 0.5 C, and charged to 0.05 C at a constant voltage of 4.4 V. The fully charged battery was placed in a hot box at 140° C. for 60 min. The battery passed the test if no fire or explosion occurred. At fixed positions in the hot box, five batteries in each Example or Comparative Example were tested, and the number of batteries that passed the test was recorded.

3) Storage Swelling Test

The battery was discharged to 4.4 V at a current of 0.5 C at 25° C., charged to 4.4 V at a current of 0.5 C, and charged to a current of 0.05 C at a constant voltage of 4.4 V. The thickness of the fully charged battery was measured with a flat-plate low-load thickness gauge under a load of 700 g and recorded as $a_1$. The battery was placed in an oven at 60° C. and stored for 21 days (21 d) at 60° C. The thickness after 21 days was tested and recorded as $b_1$. The thickness swelling ratio of the battery was calculated by the following formula: $(b1-a1)/a1 \times 100\%$.

4) Storage Impedance Test

The battery was discharged to 4.4 V at a current of 0.5 C at 25° C., charged to 4.4 V at a current of 0.5 C, and charged to a current of 0.05 C at a constant voltage of 4.4 V. The battery was placed in an oven at 60° C., and stored for 21 days at 60° C. The resistance after storage was monitored by a resistivity meter and recorded.

3. Physical and Chemical Test Methods for Lithium Ion Batteries

1) Cu Ion Test

The battery was discharged to 2.8 V at a current of 0.5 C, was allowed to stand for 5 min, discharged to 2.8 V at a current of 0.05 C, was allowed to stand for 5 min, and discharged to 2.8 V at a current of 0.01 C. The outer aluminum-plastic film was removed from the discharged battery. The electrolyte solution in the lithium ion battery was centrifuged out by a centrifuge. The centrifuged electrolyte solution was taken out, and the sample was placed in a numbered digestion tank, and weighed with an electronic scale (accurate to 0.0001 g). The sample weight was recorded as c (c≤10) g. 10 mL of concentrated $HNO_3$ (68 wt %) was slowly added, the sample on the inner wall was rinsed to the bottom of the tank, and the digestion tank was gently shaken. The water drops on the outer wall of the digestion tank were wiped off with dust-free paper, and then the digestion tank was placed in an acid removing device and digested at 180° C. for 20 min. When the solution was evaporated to 1 to 2 ml, the digestion tank was removed and cooled to room temperature. The digestion tank was washed 3 times with ultrapure water. After rinsing, the liquid was poured into a 50 ml plastic volumetric flask, diluted to the volume, and shaken fully. The sample was tested by plasma emission spectrometry (ICP) using the standard curve method, and the concentration of the test sample was recorded as $\rho_1$ g/ml. The calculation formula for Cu ions is: $(\rho_1 \times 50)/c$.

2) Ti Element Test

The battery was discharged to 2.8 V at a current of 0.5 C, was allowed to stand for 5 min, discharged to 2.8 V at a current of 0.05 C, was allowed to stand for 5 min, discharged to 2.8 V at a current of 0.01 C, allowed to stand for 5 min, and repeatedly discharged 3 times at a current of 0.01 C. The battery was disassembled by hand wearing clean gloves, and the cathode and the anode were carefully separated without touching each other. In a glove box, the cathode was soaked in high-purity DMC (dimethyl carbonate, purity≥99.99%) for 10 min, removed and air dried for 30 min. (DMC dosage: >15 ml/1540 $mm^2$ of wafer area). In a dry environment, >0.4 g of powder was scraped off using a ceramic scraper, and packaged with weighing paper. The sample was weighed with an electronic scale (accurate to 0.0001 g). The sample weight was recorded as d (d≤0.4) g. 10 mL of nitrohydrochloric acid with concentrated nitric acid and concentrated hydrochloric acid at a weight ratio of 1:1 was slowly added, the sample on the inner wall was rinsed into the bottom of the tank, and the digestion tank was gently shaken. The water drops on the outer wall of the digestion tank were wiped off with dust-free paper, and then the digestion device was assembled and digested in a microwave digestion instrument. The digestion tank was removed, the lid was washed 3 times with ultrapure water, and the washing solution was poured into the digestion tank. The sample solution was shaken, slowly poured into a funnel to flow into a volumetric flask. The digestion tank was washed 3 times, and the solution was diluted to 100 ml, and shaken well. The sample was tested by plasma emission spectrometry (ICP) using the standard curve method, and the concentration of the test sample was recorded as $\rho_2$ g/ml. The calculation formula for Ti ions is: $(\rho_2 \times 100)/d$.

A. The electrolytic solutions and lithium ion batteries of Examples 1.1-1.19 and Comparative Examples 1.1-1.4 were prepared according to the above preparation methods. The contents of the compound of Formula I and the carboxylate compound in the electrolytic solution are shown in Table 1-1.

TABLE 1-1

| No. | Compound of Formula I (wt %) | | | Carboxylate compound (wt %) | | |
|---|---|---|---|---|---|---|
|  | I-4 | I-5 | I-7 | II-1 | II-2 | III-5 |
| Example 1.1 | — | 0.1 | — | — | 5 | — |
| Example 1.2 | — | 0.2 | — | — | 5 | — |
| Example 1.3 | — | 0.3 | — | — | 5 | — |
| Example 1.4 | — | 0.5 | — | — | 5 | — |
| Example 1.5 | — | 0.7 | — | — | 5 | — |
| Example 1.6 | — | 1 | — | — | 5 | — |
| Example 1.7 | — | 2 | — | — | 5 | — |
| Example 1.8 | — | 3 | — | — | 5 | — |
| Example 1.9 | — | 0.5 | — | — | 1 | — |
| Example 1.10 | — | 0.5 | — | — | 3 | — |
| Example 1.11 | — | 0.5 | — | — | 10 | — |
| Example 1.12 | — | 0.5 | — | — | 15 | — |
| Example 1.13 | — | 0.5 | — | — | 20 | — |
| Example 1.14 | — | 0.5 | — | — | 30 | — |
| Example 1.15 | — | 0.5 | — | — | 70 | — |
| Example 1.16 | 0.5 | — | — | 10 | — | — |
| Example 1.17 | 0.5 | — | — | — | — | 10 |
| Example 1.18 | — | — | 0.5 | 10 | — | — |
| Example 1.19 | — | — | 0.5 | — | — | 10 |
| Comparative Example 1.1 | — | 0.5 | — | — | — | — |
| Comparative Example 1.2 | — | — | — | — | 10 | — |
| Comparative Example 1.3 | — | 5 | — | — | — | — |
| Comparative Example 1.4 | — | — | — | — | 80 | — |

"—" represents substance not present.

Table 1-2 shows the test results of the overcharge test, and hot box test of the lithium ion batteries in Examples 1.1-1.19 and Comparative Examples 1.1-1.4.

TABLE 1-2

| No. | Over charge test (3 C/6.5 V) | 2) Hot box test: (140° C.-60 min) |
|---|---|---|
| Example 1.1 | 4/5 pass | 4/5 pass |
| Example 1.2 | 4/5 pass | 4/5 pass |
| Example 1.3 | 5/5 pass | 5/5 pass |
| Example 1.4 | 5/5 pass | 5/5 pass |
| Example 1.5 | 5/5 pass | 5/5 pass |
| Example 1.6 | 5/5 pass | 5/5 pass |
| Example 1.7 | 5/5 pass | 5/5 pass |
| Example 1.8 | 5/5 pass | 5/5 pass |
| Example 1.9 | 5/5 pass | 5/5 pass |
| Example 1.10 | 5/5 pass | 5/5 pass |
| Example 1.11 | 5/5 pass | 5/5 pass |
| Example 1.12 | 5/5 pass | 5/5 pass |
| Example 1.13 | 5/5 pass | 5/5 pass |
| Example 1.14 | 5/5 pass | 5/5 pass |
| Example 1.15 | 5/5 pass | 5/5 pass |
| Example 1.16 | 5/5 pass | 5/5 pass |
| Example 1.17 | 5/5 pass | 5/5 pass |
| Example 1.18 | 5/5 pass | 5/5 pass |
| Example 1.19 | 5/5 pass | 5/5 pass |
| Comparative Example 1.1 | 0/5 pass | 0/5 pass |
| Comparative Example 1.2 | 1/5 pass | 1/5 pass |
| Comparative Example 1.3 | 1/5 pass | 1/5 pass |
| Comparative Example 1.4 | 2/5 pass | 2/5 pass |

From the test results of Examples 1.1-1.19 and Comparative Examples 1.1-1.4, it can be seen that the addition of both the compound of Formula I and the carboxylate compound to the electrolytic solution can significantly improve the overcharge performance and hot box performance of lithium ion batteries.

B. The electrolytic solutions and lithium ion batteries of Example 1.11 and Examples 2.1-2.12 were prepared according to the above preparation methods. The contents of the compound of Formula I, the carboxylate compound, and the compound of Formula III in the electrolytic solution are shown in Table 2-1. Table 2-1 also shows the test results of the overcharge test, and storage swelling test of the lithium ion batteries in Examples 1.11 and Comparative Examples 2.1-2.12.

TABLE 2-1

| No. | Compound I-5 (wt %) | Compound II-2 (wt %) | Compound of Formula III (wt %) III-2 | Compound of Formula III (wt %) III-3 | Over charge test (3 C/6.5 V) | Swelling rate after storage (60° C.-21 d) |
|---|---|---|---|---|---|---|
| Example 1.11 | 0.5 | 10 | — | — | 5/5 pass | 7.50% |
| Example 2.1 | 0.5 | 10 | 1 | — | 5/5 pass | 6.50% |
| Example 2.2 | 0.5 | 10 | 3 | — | 5/5 pass | 5.00% |
| Example 2.3 | 0.5 | 10 | — | 1 | 5/5 pass | 6.50% |
| Example 2.4 | 0.5 | 10 | — | 3 | 5/5 pass | 5.00% |
| Example 2.5 | 0.3 | 5 | 2 | — | 5/5 pass | 6.20% |
| Example 2.6 | 0.5 | 15 | 2 | — | 5/5 pass | 5.80% |
| Example 2.7 | 0.5 | 20 | 2 | — | 5/5 pass | 5.70% |
| Example 2.8 | 0.3 | 20 | 2 | — | 5/5 pass | 5.90% |
| Example 2.9 | 0.3 | 5 | — | 2 | 5/5 pass | 6.10% |
| Example 2.10 | 0.5 | 15 | — | 2 | 5/5 pass | 5.70% |
| Example 2.11 | 0.5 | 20 | — | 2 | 5/5 pass | 5.60% |
| Example 2.12 | 0.3 | 20 | — | 2 | 5/5 pass | 5.80% |

"—" represents substance not present.

It can be seen from the test results of Examples 2.1-2.12 and Example 1.11 that adding the compound of Formula III to the electrolytic solution containing the compound of Formula I and the carboxylate compound can significantly reduce the storage swelling rate of lithium ion batteries. This may be attributed to the fact that the compound of Formula I, the carboxylate compound and the compound of Formula III work together to further reduce the risk of oxidation of the electrolytic solution, and also improve the protection for the cathode and reduce the direct contact between the cathode active material interface and the electrolytic solution, thereby alleviating the swelling caused by the contact between the electrolytic solution and the cathode active material during high-temperature storage.

C. The electrolytic solutions and lithium ion batteries of Example 1.11 and Examples 3.1-3.7 were prepared according to the above preparation methods. The contents of the compound of Formula I, the carboxylate compound, and the lithium salt additive in the electrolytic solution are shown in Table 3-1. Table 3-1 also shows the test results of the hot box test, and storage impedance test of lithium ion batteries in Example 1.11 and Examples 3.1-3.7.

TABLE 3-1

| No. | Compound I-5 (wt %) | Compound II-2 (wt %) | LiPO$_2$F$_2$ (wt %) | Hot box test (140° C.-60 min) | Storage impedance at 60° C. for 21 d (mΩ) |
|---|---|---|---|---|---|
| Example 1.11 | 0.5 | 10 | — | 5/5 pass | 27.2 |
| Example 3.1 | 0.5 | 10 | 0.1 | 5/5 pass | 27.0 |
| Example 3.2 | 0.5 | 10 | 0.3 | 5/5 pass | 25.7 |
| Example 3.3 | 0.5 | 10 | 0.5 | 5/5 pass | 26.4 |
| Example 3.4 | 0.3 | 5 | 0.3 | 5/5 pass | 26.2 |
| Example 3.5 | 0.5 | 15 | 0.3 | 5/5 pass | 26.1 |
| Example 3.6 | 0.5 | 20 | 0.3 | 5/5 pass | 26.0 |
| Example 3.7 | 0.3 | 20 | 0.3 | 5/5 pass | 26.2 |

"—" represents substance not present.

It can be seen from the test results of Examples 3.1-3.7 and Example 1.11 that adding the lithium salt additive $LiPO_2F_2$ to the electrolytic solution containing the compound of Formula I and the carboxylate compound can significantly reduce storage impedance of lithium ion batteries. This may be because the compound of Formula I, the carboxylate compound and $LiPO_2F_2$ work together to increase the LiF component in the organic protective film, which enhances the stability of the organic protective film, improves the resistance to high temperature, and thus improves storage impedance.

D. The electrolytic solutions and lithium ion batteries of Example 1.11 and Examples 4.1-4.9 were prepared according to the above preparation methods. The contents of related compounds in the electrolytic solution are shown in Table 4-1. Table 4-1 also shows the test results of the overcharge test, and storage impedance test of the lithium ion batteries in Examples 1.11 and Comparative Examples 4.1-4.9.

TABLE 4-1

| No. | Compound I-5 (wt %) | Compound II-2 (wt %) | Cu ion (ppm) | Overcharge test (3 C/6.5 V) | Storage impedance test (60° C.-21 d(mΩ)) |
|---|---|---|---|---|---|
| Example 1.11 | 0.5 | 10 | 4 | 5/5 pass | 27.2 |
| Example 4.1 | 0.5 | 10 | 1 | 5/5 pass | 30.0 |
| Example 4.2 | 0.5 | 10 | 5 | 5/5 pass | 27.0 |
| Example 4.3 | 0.5 | 10 | 10 | 5/5 pass | 26.4 |
| Example 4.4 | 0.5 | 10 | 20 | 5/5 pass | 26.7 |
| Example 4.5 | 0.5 | 10 | 30 | 5/5 pass | 27.1 |
| Example 4.6 | 0.3 | 5 | 5 | 5/5 pass | 27.6 |
| Example 4.7 | 0.5 | 15 | 7 | 5/5 pass | 26.5 |
| Example 4.8 | 0.5 | 20 | 8 | 5/5 pass | 26.4 |
| Example 4.9 | 0.3 | 20 | 6 | 5/5 pass | 26.8 |

"—" represents substance not present.

During the preparation of lithium-ion batteries, the batteries after injecting electrolytic solution were allowed to stand at high temperature. The electrolytic solution in the lithium-ion battery resulted in some chemical reactions during this process, and trace Cu metal impurities in the anode of the lithium-ion battery were dissolved out. The trace Cu ions enhanced the conductivity of the electrolytic solution, thereby reducing the impedance. It can be seen from the test results of Examples 4.1-4.9 and Example 1.11 that including a suitable amount of Cu ions in the electrolytic solution containing the compound of Formula I and the carboxylate compound can significantly reduce the storage impedance of lithium ion batteries.

E. The electrolytic solutions and lithium ion batteries of Examples 1.11 and 5.1-5.10 were prepared according to the above preparation method. Table 5-1 shows the contents of relevant substances in the electrolytic solutions of Example 1.11 and Examples 5.1-5.10, the content of the Ti element in the cathode active material layer and the test results of the hot box test.

TABLE 5-1

| No. | Compound I-5 (wt %) | Compound II-2 (wt %) | Ti element (ppm) | Hot box test (140° C.-60 min) |
|---|---|---|---|---|
| Example 1.11 | 0.5 | 10 | 400 | 5/5 pass |
| Example 5.1 | 0.5 | 10 | 100 | 1/5 pass |
| Example 5.2 | 0.5 | 10 | 200 | 2/5 pass |
| Example 5.3 | 0.5 | 10 | 300 | 3/5 pass |
| Example 5.4 | 0.5 | 10 | 500 | 5/5 pass |
| Example 5.5 | 0.5 | 10 | 600 | 5/5 pass |
| Example 5.6 | 0.5 | 10 | 800 | 5/5 pass |
| Example 5.7 | 0.3 | 5 | 500 | 5/5 pass |
| Example 5.8 | 0.5 | 15 | 500 | 5/5 pass |
| Example 5.9 | 0.5 | 20 | 500 | 5/5 pass |
| Example 5.10 | 0.3 | 20 | 500 | 5/5 pass |

The cathode active material includes the Ti element, which can not only enhance the interface contact between the cathode active material and the electrolytic solution, but also stabilize the oxygen radicals in the cathode active material, so as to reduce the contact between oxygen radicals and the electrolytic solution, and reduce the oxidation reaction between the cathode active material and the electrolytic solution. Oxygen radicals will accelerate the catalytic oxidation of the electrolytic solution, especially during safety tests. In the subject application, a combination of the compound of Formula I and fluorocarboxylate was used, which has a certain protective effect on the cathode interface, and has enhanced oxidation resistance, and further reduces the reaction of the cathode active material with the electrolyte solution in combination with the doped Ti element, thereby achieving the effect of improving hot box safety. It can be seen from the test results of Example 1.11 and Example 5.1-5.10 that with the amount of Ti doped increasing, the improvement effect of the hot box performance is significant.

F. The electrolytic solutions and lithium ion batteries of Examples 1.11 and 6.1-6.3 were prepared according to the above preparation method. Table 6-1 shows the contents of relevant substances in the electrolytic solutions of Example 1.11 and Examples 6.1-6.3.

TABLE 6-1

| No. | Compound I-5 (wt %) | Compound II-2 (wt %) | Compound III-3 (wt %) | $LiPO_2F_2$ (wt %) | Cu ion (ppm) | Ti element (ppm) |
|---|---|---|---|---|---|---|
| Example 1.11 | 0.5 | 10 | — | — | 7 | 400 |
| Example 6.1 | 0.5 | 10 | 1 | 0.2 | 7 | 400 |
| Example 6.2 | 0.5 | 10 | 2 | 0.3 | 8 | 500 |
| Example 6.3 | 0.5 | 10 | 2 | 0.5 | 5 | 500 |

"—" denotes that the substance is not present.

Table 6-2 shows the test results of the overcharge test, hot box test, storage swelling test and storage impedance test of the lithium ion batteries in Example 1.11 and Examples 6.1-6.3.

TABLE 6-2

| No. | Overcharge test (3 C/6.5 V) | Hot box test (140° C.-60 min) | Swelling rate after storage (60° C.-21 d) | Storage impedance test (60° C-21 d(mΩ)) |
|---|---|---|---|---|
| Example 1.11 | 5/5 pass | 5/5 pass | 7.50% | 27.2 |
| Example 6.1 | 5/5 pass | 5/5 pass | 6.50% | 26.8 |
| Example 6.2 | 5/5 pass | 5/5 pass | 6.20% | 26.5 |
| Example 6.3 | 5/5 pass | 5/5 pass | 6.10% | 26.6 |

It can be seen from the test results of Example 1.11 and Examples 6.1-6.3 that when the trinitrile compound and $LiPO_2F_2$ are added to the electrolytic solution containing the compound of Formula I and the carboxylate compound, the cathode active material layer contains an appropriate amount of the Ti element, and the content of the Cu ions in the electrolytic solution is within a certain range, the overcharge performance and hot box performance of the lithium ion battery can be significantly improved, and the storage swelling rate and storage impedance can be significantly reduced.

Throughout the specification, references to "some embodiments", "part of embodiments", "one embodiment", "another example", "example", "specific example" or "part of examples" mean that at least one embodiment or example of the present application includes specific features, structures, materials or characteristics described in the embodiment or example. Thus, the descriptions that appear throughout the specification, such as "in some embodiments", "in an embodiment", "in one embodiment", "in another example", "in an example", "in a particular example" or "for example" are not necessarily the same embodiment or example in the application. Furthermore, the specific features, structures, materials or characteristics in the descriptions can be combined in any suitable manner in one or more embodiments or examples.

Although illustrative embodiments have been shown and described, it should be understood by those skilled in the art that the above embodiments cannot be interpreted as limitations to the present application, and the embodiments can be changed, substituted and modified without departing from the spirit, principle and scope of the present application.

The above-described embodiments of the present application are intended to be illustrative only. Numerous alternative embodiments may be devised by a person skilled in the art without departing from the scope of the following claims.

What is claimed is:

1. An electrolytic solution, comprising: a compound of Formula I, a carboxylate compound, and a compound of Formula III, wherein the compound of Formula I comprises at least one of:

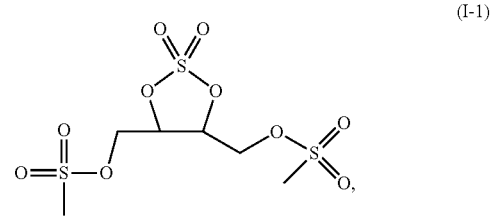

(I-1)

-continued (I-2) [structure: cyclic sulfate with phenyl substituent]

(I-3) [structure: cyclic sulfate fused to tetrahydropyran]

(I-4) [structure: cyclic sulfate with CH2-O-phenyl-CN substituent]

(I-5) [structure: bis-cyclic sulfate]

(I-6) [structure: bis-cyclic sulfate with dioxolane groups]

(I-7) [structure: cyclic sulfate with F substituent] or (I-8) [structure: cyclic sulfate with CF3 substituent];

the carboxylate compound comprises at least one of:

(II-1) [structure: propionate ester with CH2CHF2]

(II-2) [structure: acetate ester with CH2CHF2]

(II-3) [structure: propionate ester with CH2CF3]

(II-4) [structure: acetate ester with CH2CF3], or (II-5) [structure: acetate ester with CH2CH2F];

the compound of Formula III comprises at least one of:

(Formula III-1) [structure: tris(2-cyanoethyl)methane-like: NC-CH2CH2-CH(CH2CH2CN)-CH2CH2CN]

(Formula III-2) [structure: branched tetranitrile with four CN groups]

(Formula III-3) [structure: NC-CH2CH2-O-CH2-CH(O-CH2CH2CN)-CH2-O-CH2CH2CN] or (Formula III-4) [structure: C(CH2CN)4 - tetracyanomethylmethane]

and
a weight percentage of the compound of formula I, a wt %, is 0.1 wt % to 3 wt % based on a total weight of the electrolytic solution, a weight percentage of the carboxylate compound, b w %, is 1 wt % to 50 wt % based on the total weight of the electrolytic solution, and a weight percentage of the compound of Formula III is 0.1 wt % to 4 wt % based on the total weight of the electrolytic solution.

2. The electrolytic solution according to claim 1, further comprising a lithium salt additive, including at least one of LiPO$_2$F$_2$, lithium bis(trifluoromethanesulphonyl)imide, lithium bis(fluorosulfonyl)imide, lithium bis(oxalate)borate, lithium tetrafluorophosphate xalate, lithium difluoro(oxalate)borate or lithium hexafluorocesate,
wherein a weight percentage of the lithium salt additive is 0.001-5 wt % based on a total weight of the electrolytic solution.

3. An electrochemical device, comprising an anode; a cathode, having a cathode active material layer comprising a cathode active material; and the electrolytic solution according to claim 1.

4. The electrochemical device according to claim 3, wherein the anode further comprises a current collector comprising copper, and after charging, the electrolytic solution of the electrochemical device further comprises copper ions, and a content of the copper ions is 0.01-50 ppm based on a total weight of the electrolytic solution.

5. The electrochemical device according to claim 3, wherein the cathode active material comprises a lithium metal oxide including a Ti element, and a content of the Ti element is $t \times 10^2$ ppm based on a total weight of the cathode active material layer, wherein t is 2-10, and meets $(a+b)/t \leq 35$.

6. An electronic device, comprising the electrochemical device according to claim 3.

7. The electronic device of claim 6, wherein the anode further comprises a current collector comprising copper, and after charging, the electrolytic solution of the electrochemical device further comprises copper ions, and a content of the copper ions is 0.01-50 ppm based on a total weight of the electrolytic solution.

8. The electronic device of claim 6, wherein the cathode active material comprises a lithium metal oxide including a Ti element, and a content of the Ti element is $t \times 10^2$ ppm based on the total weight of the cathode active material layer, wherein t is 2-10, and meets $(a+b)/t \leq 35$.

* * * * *